(12) United States Patent
Markin

(10) Patent No.: US 8,871,497 B2
(45) Date of Patent: Oct. 28, 2014

(54) DEVICE AND METHOD FOR AUTOMATING MICROBIOLOGY PROCESSES

(75) Inventor: Rodney S. Markin, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 1222 days.

(21) Appl. No.: 12/013,746

(22) Filed: Jan. 14, 2008

(65) Prior Publication Data

US 2009/0181449 A1     Jul. 16, 2009

(51) Int. Cl.
| | |
|---|---|
| *C12M 1/34* | (2006.01) |
| *C12M 3/00* | (2006.01) |
| *C12M 1/00* | (2006.01) |
| *C12M 3/06* | (2006.01) |
| *C12M 1/40* | (2006.01) |
| *C12M 1/36* | (2006.01) |
| *C12M 1/24* | (2006.01) |
| *C12M 1/32* | (2006.01) |
| *G01N 35/04* | (2006.01) |
| *B01L 3/00* | (2006.01) |

(52) U.S. Cl.
CPC .............. *C12M 41/48* (2013.01); *C12M 23/50* (2013.01); *C12M 23/28* (2013.01); *C12M 27/14* (2013.01); *C12M 23/40* (2013.01); *C12M 21/18* (2013.01); *G01N 2035/0481* (2013.01); *C12M 23/54* (2013.01); *C12M 23/34* (2013.01); *G01N 35/04* (2013.01); *C12M 23/08* (2013.01); *B01L 3/5027* (2013.01); *C12M 23/52* (2013.01); *G01N 2035/0479* (2013.01); *C12M 33/06* (2013.01); *C12M 23/42* (2013.01); *C12M 23/44* (2013.01); *C12M 23/58* (2013.01)
USPC .................. 435/287.3; 435/287.1; 435/294.1; 703/11

(58) Field of Classification Search
CPC . B01L 7/52; B01L 2200/147; B01L 3/50851; B01L 2300/0636; C12M 41/48; C12M 41/14; C12M 1/3446; C12M 23/08; C12M 23/34; C12M 21/04; C12M 1/14; G01N 35/025; G01N 35/00029; G01N 33/54366; G01N 33/54373; B01J 2219/00722; B01J 2219/00659; B01J 19/0046; C40B 40/06; Y02E 50/343; B82Y 30/00
USPC .......... 435/286.1, 287.1, 287.2, 287.3, 294.1; 700/11
See application file for complete search history.

(56) References Cited

U.S. PATENT DOCUMENTS 3,532,469 A * 10/1970 Vicario ........................... 422/65
4,056,359 A    11/1977 Janin
(Continued)

FOREIGN PATENT DOCUMENTS

| DE | 39 34 890 A1 | 4/1990 |
|---|---|---|
| EP | 1 548 099 A1 | 6/2005 |

(Continued)

OTHER PUBLICATIONS

European Patent Office, International Search Report with respect to PCT/US2009/030600 (Nov. 23, 2011).

(Continued)

*Primary Examiner* — Michael Hobbs
(74) *Attorney, Agent, or Firm* — Leydig, Voit & Mayer, Ltd.

(57) ABSTRACT

A device and method for automating the handling and testing of microbiological specimens are provided. A portable specimen collection vehicle (SCV) is provided which comprises a protective housing, a specimen chamber for receiving a biospecimen sample, a plurality of culturing chambers each for receiving a portion of the biospecimen sample and each containing a different culture medium, a system of fluid ducts connecting the specimen chamber to each of the culturing chambers, and an actuator that facilitates flow of portions of the biospecimen sample from the specimen chamber through the system of fluid ducts and into each of the culturing chambers, wherein biological organisms in the biospecimen begin to grow in one or more of the culturing chambers and cultured portions of the biospecimen sample can be withdrawn selectively from the apparatus.

22 Claims, 6 Drawing Sheets

(56) References Cited

U.S. PATENT DOCUMENTS

| | | |
|---|---|---|
| 4,072,577 A | 2/1978 | Hirshaut |
| 4,209,585 A | 6/1980 | Lloyd et al. |
| 4,250,266 A | 2/1981 | Wade |
| 4,805,469 A | 2/1989 | Commarmot |
| 4,810,388 A * | 3/1989 | Trasen .................. 210/638 |
| 5,087,423 A | 2/1992 | Ishibashi |
| 5,351,801 A | 10/1994 | Markin et al. |
| 5,366,062 A | 11/1994 | Markin et al. |
| 5,370,215 A | 12/1994 | Markin et al. |
| 5,377,813 A | 1/1995 | Markin et al. |
| 5,402,875 A | 4/1995 | Markin et al. |
| 5,417,922 A | 5/1995 | Markin et al. |
| 5,427,743 A | 6/1995 | Markin |
| 5,519,635 A * | 5/1996 | Miyake et al. ............ 700/285 |
| 5,529,166 A | 6/1996 | Markin et al. |
| 5,589,137 A | 12/1996 | Markin et al. |
| 5,612,188 A | 3/1997 | Shuler et al. |
| 5,614,415 A | 3/1997 | Markin |
| 5,660,998 A | 8/1997 | Naumann et al. |
| 5,941,366 A | 8/1999 | Quinlan et al. |
| 5,985,670 A | 11/1999 | Markin |
| 5,998,202 A | 12/1999 | Schwarz et al. |
| 6,122,396 A | 9/2000 | King et al. |
| 6,177,050 B1 | 1/2001 | Bybee et al. |
| 6,197,255 B1 * | 3/2001 | Miyake et al. ................ 422/64 |
| 6,558,946 B1 | 5/2003 | Krishnamurthy |
| 6,686,173 B2 | 2/2004 | Bochner et al. |
| 2003/0022363 A1 * | 1/2003 | Rao et al. .................. 435/293.1 |
| 2005/0276728 A1 * | 12/2005 | Muller-Cohn et al. ....... 422/102 |
| 2006/0160205 A1 * | 7/2006 | Blackburn et al. ......... 435/287.2 |
| 2006/0263258 A1 | 11/2006 | Harris et al. |
| 2007/0077615 A1 | 4/2007 | Gillis |

FOREIGN PATENT DOCUMENTS

| | | |
|---|---|---|
| FR | 2 600 166 A1 | 12/1987 |
| WO | WO 93/24234 A2 | 12/1993 |
| WO | WO 94/15219 A1 | 7/1994 |

OTHER PUBLICATIONS

Ikeda et al., "Total Clinical Laboratory Testing System for Laboratory Automation," *Hitachi Review*, 41(4): 167-172 (Sep. 1992).

Markin, "Implementing automation in a modern clinical laboratory," *Chemometrics and Intelligent Laboratory Systems: Laboratory Information Management*, 21(2/3): 169-179 (Dec. 1993).

\* cited by examiner

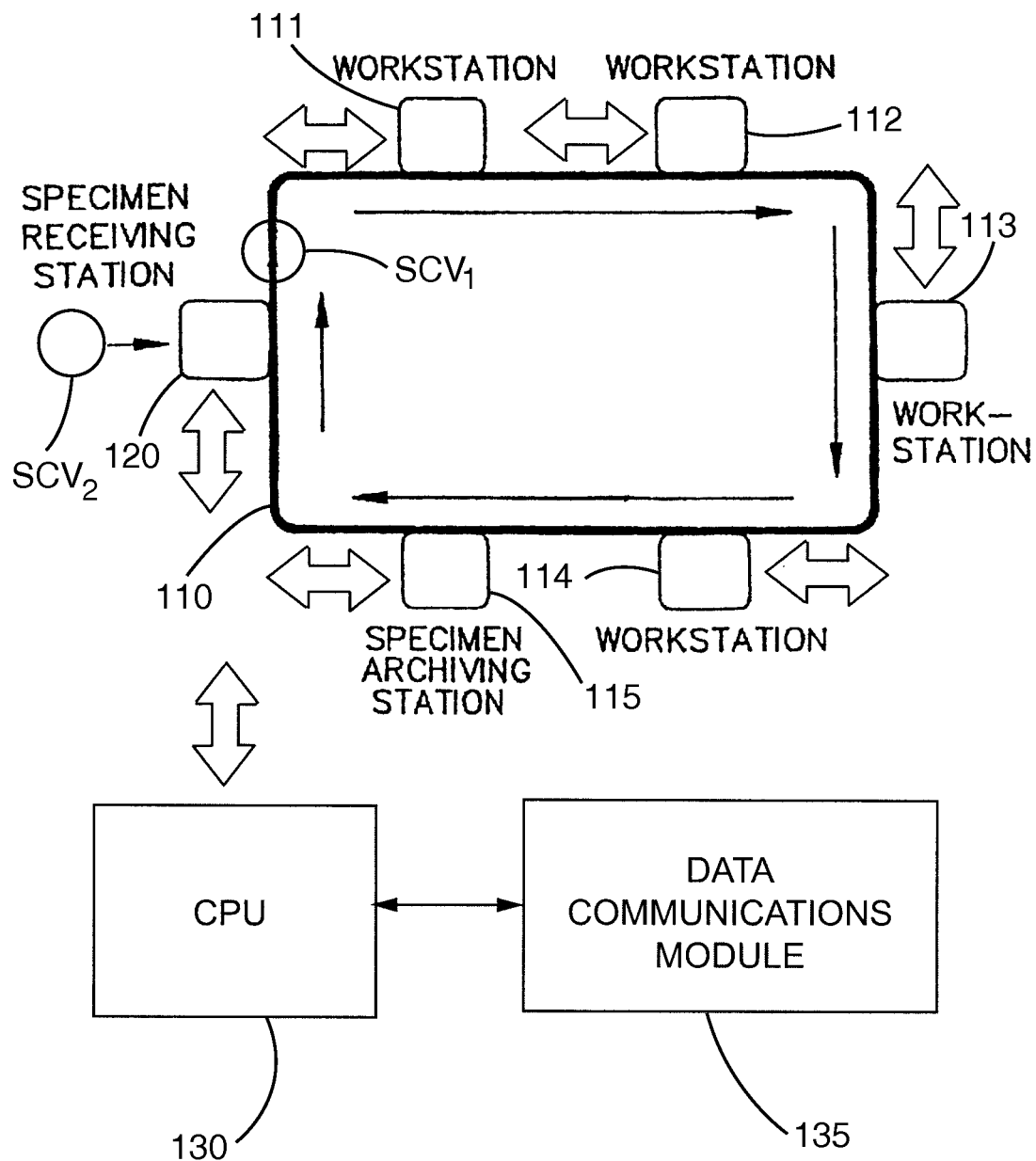

DEVICE AND METHOD FOR AUTOMATING MICROBIOLOGY PROCESSES

STATEMENT REGARDING FEDERALLY SPONSORED RESEARCH AND DEVELOPMENT

This invention was made with government support under grant No. W81XWH-04-1-0910 awarded by the Department of Defense. The government has certain rights in the invention.

TECHNICAL FIELD

The present invention relates generally to laboratory automation, and more particularly to a device and method for automating the collection, handling and testing of microbiological specimens.

BACKGROUND OF THE INVENTION

Multiple collection devices for the procurement of specimens to be analyzed in a clinical microbiology laboratory exist. These devices are typically designed so that different types of microorganisms can be retrieved and identified from the source from which the specimens are collected (blood, sputum, urine, stool, etc.). Adapted to the current setting of manual processing in the microbiology laboratory, these devices are not adequate for processing on an automated platform.

In the identification of pathogenic organisms in a clinical setting, a significant issue is decreasing the turnaround time from specimen collection to results reporting. This is true especially in a situation of biological contamination or in the field. A lot of the specimen preparation time is spent in the growth and concentration of the pathogens to be identified. In order to reduce this time, it is advantageous to start the growth phase as soon as the specimen is collected. Positive specimen identification is imperative to ensure the quality of the results reported on each and every specimen.

The automation of the clinical microbiology laboratory requires a standard device that can be integrated easily into the process of specimen collection and in the automated processing of identification of pathogen(s) and determination of the appropriate antibiotic therapy. Today, no standard device for medical microbiology exists. The invention described here addresses these and related needs.

BRIEF SUMMARY OF THE INVENTION

Various aspects of devices and techniques for specimen carriers and for automatic testing of laboratory specimens are described in the following US patents, herein incorporated in their entireties by reference: U.S. Pat. No. 5,417,922; U.S. Pat. No. 5,427,743; U.S. Pat. No. 5,589,137; U.S. Pat. No. 5,614,415; and U.S. Pat. No. 5,985,670.

It is a general object of the present invention to provide a device and an automated method to reduce the reliance on human labor to conduct the analysis of microbiological specimens submitted for culture, identification and sensitivity. The device and method of the present invention can be used for clinical, biohazard, biosecurity, agricultural, environmental and food microbiology applications. The device and method can be applied to all microbiology specimens. For example, the device and method of the present invention can be used with microbiological specimens including, but not limited to, bacteria, viruses, fungi, mycobacteria, archae, protists, prions, and acidobacter. The specimens can be collected from a variety of sources. For example, specimens may be collected from a patient, also referred to herein as "subject," either human or non-human.

The device, referred to herein as a "Specimen Culture Vehicle (SCV)," which in one aspect is a culture engine for microorganisms, is manually labeled with a unique patient identification code (e.g., number), as well as a device serial number and a specimen (accession) number representing the ordering event. The SCV can also be labeled with a barcode identification, a radio frequency identification tag (RFID), or both simultaneously.

Culturing microorganisms according to this invention is initiated as soon as possible, preferably at the point of collection. The culture of microorganisms that is initiated at the point of collection continues in the SCV, in a temperature-controlled culture engine at a desired temperature (e.g., approximately 37° C.), humidity and with aerobic and anaerobic conditions, and thus microorganism growth occurs during transport to the laboratory. This shortens the receipt-to-result phase in the laboratory. The transport time will vary depending upon the application (i.e., clinical, agricultural, biohazard, etc) and the distance to the automation platform. When the culture engine and its contents arrive in the laboratory, the specimen is evaluated for growth using either turbidimetry measurements or other means of growth determination.

After adequate growth is determined, the specimen is subjected to analysis using one or more analytical methods. Preferably, the specimen is subjected to a plurality of methods, such as distribution to standard agar plates, distribution to polymerase chain reaction (PCR) methodology, distribution to chromatography methods (e.g., gas and/or liquid chromatography), and distribution to mass spectrometry methods. Using mass spectrometry, the specimen can be analyzed much sooner in the growth process than with conventional culture due to the sensitivity of the technology/method. The specificity of the analysis will allow the differentiation between pathogens and normal flora based upon the specimen source, specimen type and the estimated concentration (a measurement analogous to culture counts).

The methods of the present invention provide a decrease in turnaround in culture results reporting in a clinical setting, which can decrease the length of stay of patients and allow antibiotic adjustments to be made earlier in the course of treatment. In one example, the method steps start after the collection of the specimen, which would be the same collection method as currently used in the art (e.g., swab, blood, stool, urine, etc.). The specimen is placed into a culture engine that immediately begins the culture of the materials/specimens submitted. In the case of a specimen that requires some pre-processing, such as tissue or solids, a pre-processing step can be used prior to introduction of the specimen into the culture engine. In the culture engine, there is a plurality of different culturing chambers, each containing a different type of growth (culturing) media. Preferably, there are eight different chambers in the culture engine. If the different growth media are selected carefully, over 98% of known bacteria, viruses, fungi and mycobacterium will grow in at least one of these eight different types of media.

BRIEF DESCRIPTION OF THE DRAWINGS

FIG. 6 illustrates a schematic embodiment of a Microbiology Automation Platform (MAP) that utilizes an SCV.

DETAILED DESCRIPTION OF THE PREFERRED EMBODIMENTS

Figure 1:
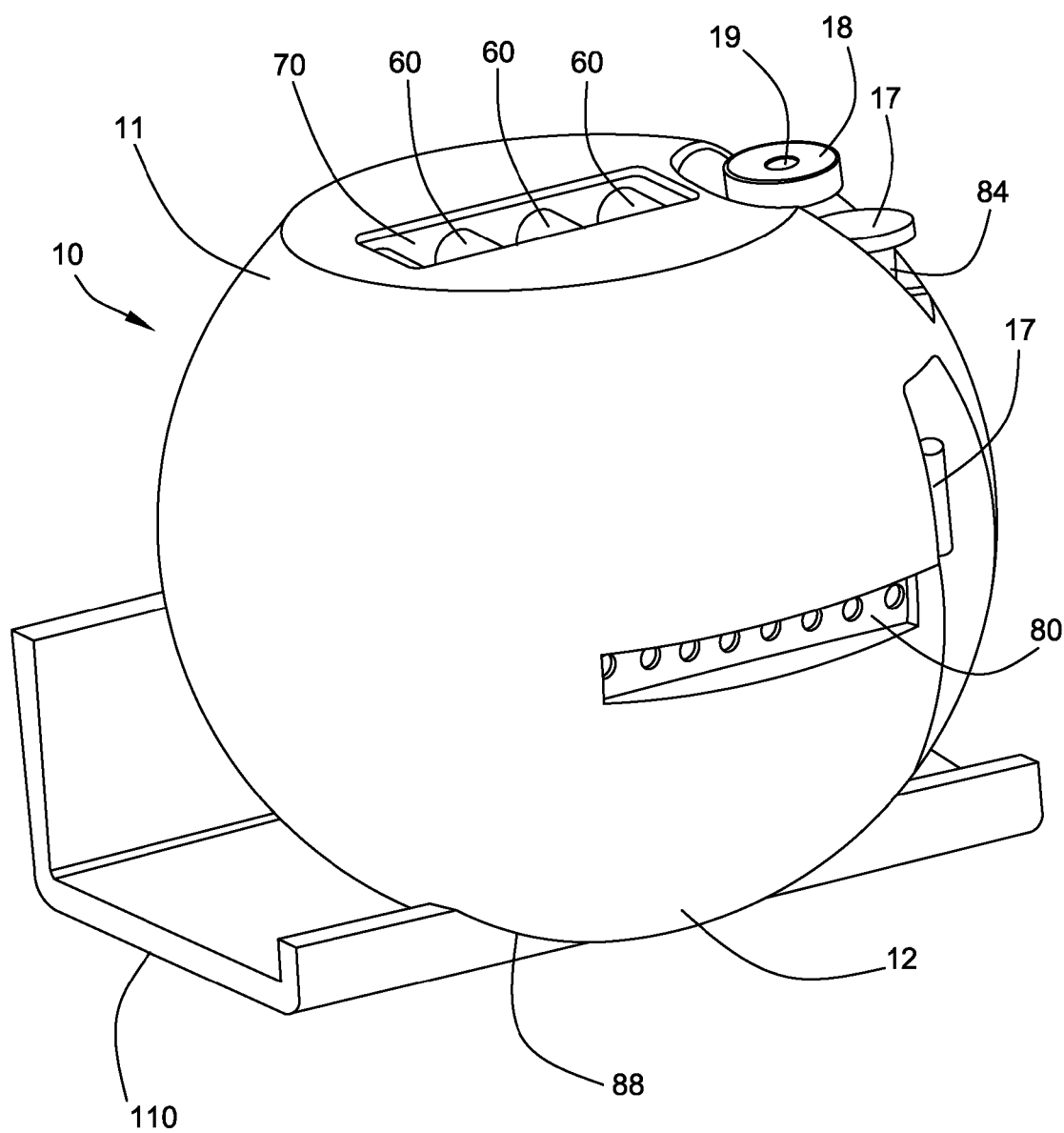
FIG. 1 illustrates a first top perspective view of one embodiment of a Specimen Culture Vehicle (SCV).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventor for carrying out the invention. Variations of those preferred embodiments may become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. Unless defined otherwise, all technical and scientific terms used herein have the meaning commonly understood by a person skilled in the art to which this invention belongs.

The Specimen Culture Vehicle (SCV) for microbiology specimens of the present invention is an automated device, which in one aspect is designed to be used as a component of a Microbiology Automation Platform (MAP), described below. The SCV and the MAP can be integrated to physically process specimens facilitated by a software scheduling and routing system through a series of steps involving: (i) pre-identification; (ii) identification; and (iii) post-identification processing of the specimen. The pre-identification can include, but is not limited to, growth and isolation, fixation, amplification, separation, and staining. The identification phase can include, but is not limited to, visual inspection and identification, UV/visible and mass spectrometry, enzyme-linked immunosorbent assay (ELISA), immunoassay, and other biochemical methodologies. The post-identification phase can include, but is not limited to, holding for additional testing, storage, retrieval, and archiving.

Figure 2:
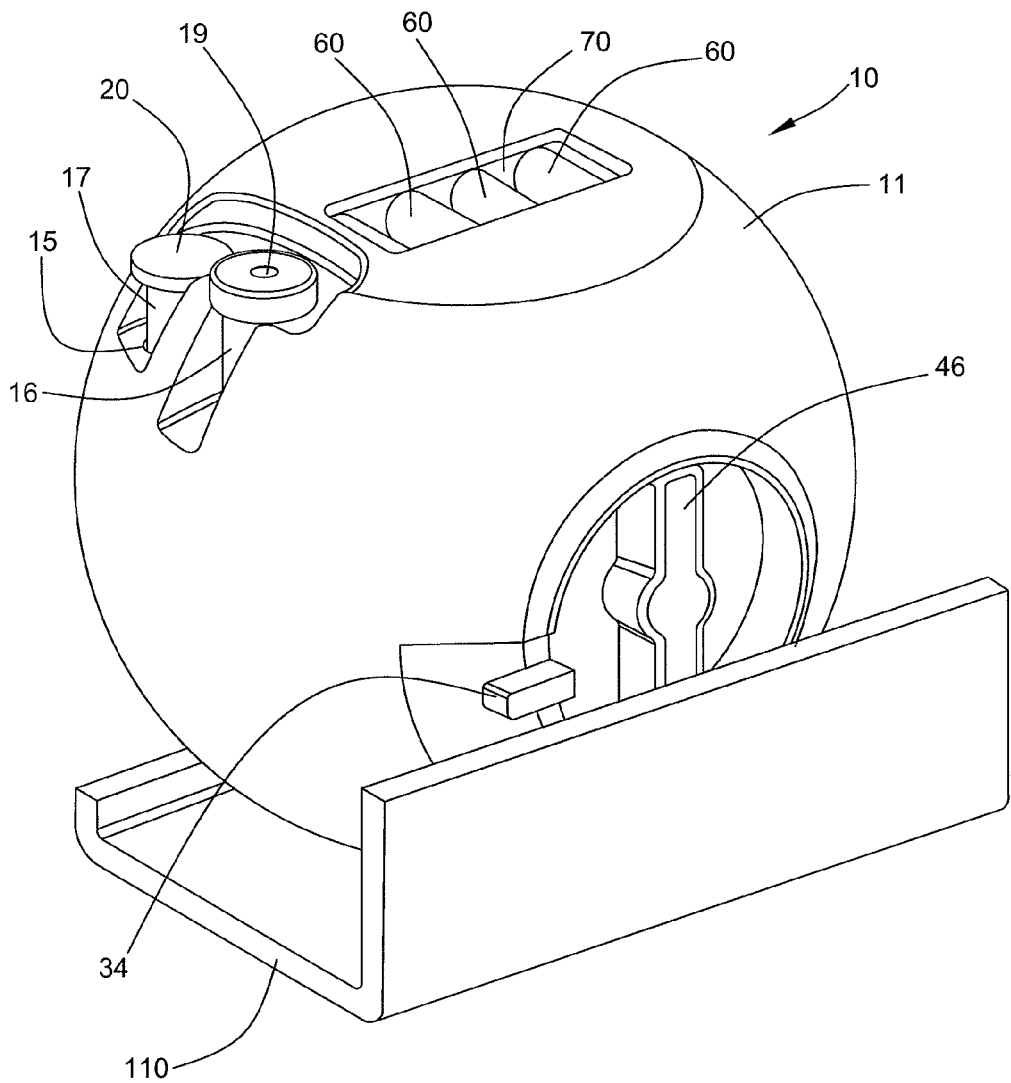
FIG. 2 illustrates a second top perspective view of the SCV shown in FIG. 1.
Figure 3:
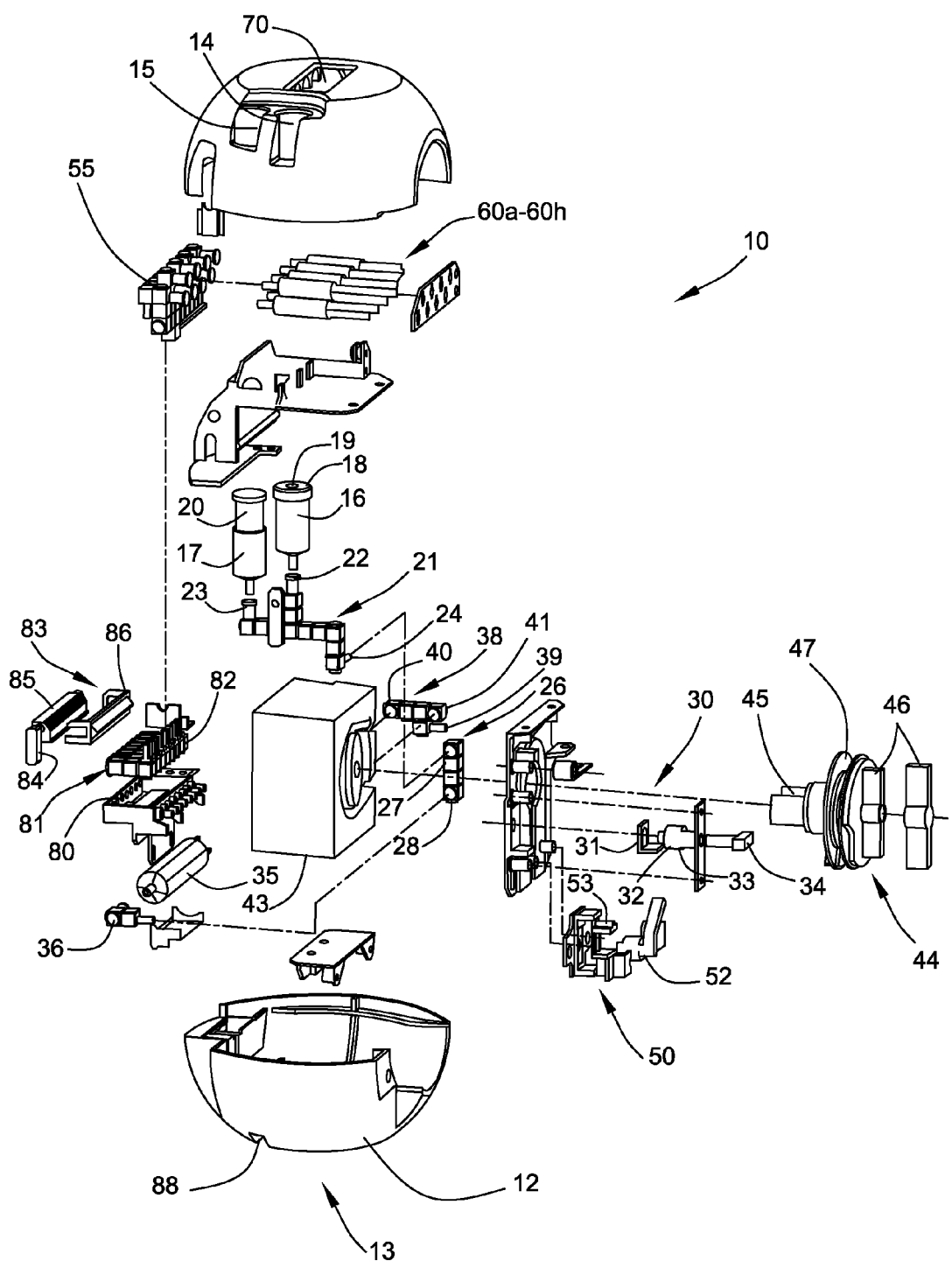
FIG. 3 illustrates an exploded view of the SCV shown in FIGS. 1 and 2.

Shown in FIGS. 1-3 is one embodiment of a Specimen Culture Vehicle (SCV) device for microbiology specimens, in both assembled and exploded views. In this embodiment, the SCV 10 is shown to include a housing comprising a top shell 11 and a bottom shell 12. Preferably, the overall shape of the SCV housing is spherical, the diameter of which is preferably smaller than 8.9 cm. The SCV is preferably designed to fit in a typical hospital pneumatic tube transport system, and also to fit in a standard-sized biohazard transport bag. The bottom surface 13 of the housing is molded generally flat so that the SCV remains upright, and is not subject to tipping over. Because of its flat top and bottom surfaces, the SCV is stackable and rackable. The integrity of the media, diluent, and specimen is maintained while held in the SCV regardless of the physical orientation of the SCV.

The SCV's "shell" housing is preferably constructed of rigid plastic (for example, polycarbonate), and more preferably of injection molded plastic. As such, it is designed to protect the inoculated growth chambers in case of impact or if the SCV is dropped. Moreover, the SCV's physical composition is designed to withstand cleaning with standard laboratory cleaning solutions, and is designed to withstand adverse environmental conditions of temperature, humidity, stress, air particulates, and pressure. The SCV material should preferably withstand temperatures of about 0° C. to about 50° C. and a relative humidity of about 15% to about 80% for about 180 days, while maintaining specimen integrity and preventing leakage, evaporation, desiccation or aerosolization of the specimen, media, or diluent(s). The SCV physical composition should preferably support storage temperatures post-analysis of about 4° C. to about 8° C. for about 1 week.

The SCV construction materials are chosen so that they will maintain the integrity of the media and organisms to be isolated. The SCV should withstand the range of mechanical forces and pressures to which it reasonably can be expected to be subjected without breakage or leakage. Moreover, the materials selected for the SCV structure, including its mechanisms, seals, and gaskets, should not interfere (chemically or otherwise) with the internal mechanisms, seals, growth media or microbiological specimen. Nor should the materials selected for the seals and gaskets degrade significantly within the shelf life of the SCV. Preferably, the plastic structure should be able to have adhesive labels applied to it.

The top shell 11 of the housing is formed to include a pair of exteriorly-exposed cylindrical cavities 14, 15 for respectively receiving a specimen input chamber (syringe) 16 and a diluent chamber (syringe) 17. The specimen input chamber 16 is designed to prevent leakage, aerosolization or cross-contamination, and is covered with a screw-top lid 18. The lid 18 has a permeable aperture 19 (conforming to standard industry requirements governing the use of these types of closures) that allows a needle (or canula) to penetrate it while retaining the specimen within the chamber, and preventing air and possible contaminants from entering. The lid 18 for the specimen input chamber also has some feature (not shown) that indicates if the specimen has been tampered with.

The specimen input chamber 16 is preferably clear on at least one side so that the integrity of the specimen can be observed by the operator from the exterior of the SCV. In general, the specimen input chamber 16 is large enough to accept all standard sized swabs, and it is designed to contain preferably, at minimum, 4.0 ml of liquid sample and an additional 2.0 ml of fluid in case the operator applies diluent to the chamber. The specimen input chamber is designed to account for any losses due to dead volume and/or any volume changes due to temperature changes.

The diluent chamber 17 contains a diluent (preferably about 2.0 ml of 0.9% saline) that can be added to the specimen. A finger-operated plunger 20 permits the operator to apply a selective amount of the diluent to the specimen input chamber 16. The diluent chamber 17 is designed to account for losses due to dead volume and volume changes due to temperature changes, and is designed to prevent leakage, aerosolization, tampering or cross-contamination.

Figure 4:
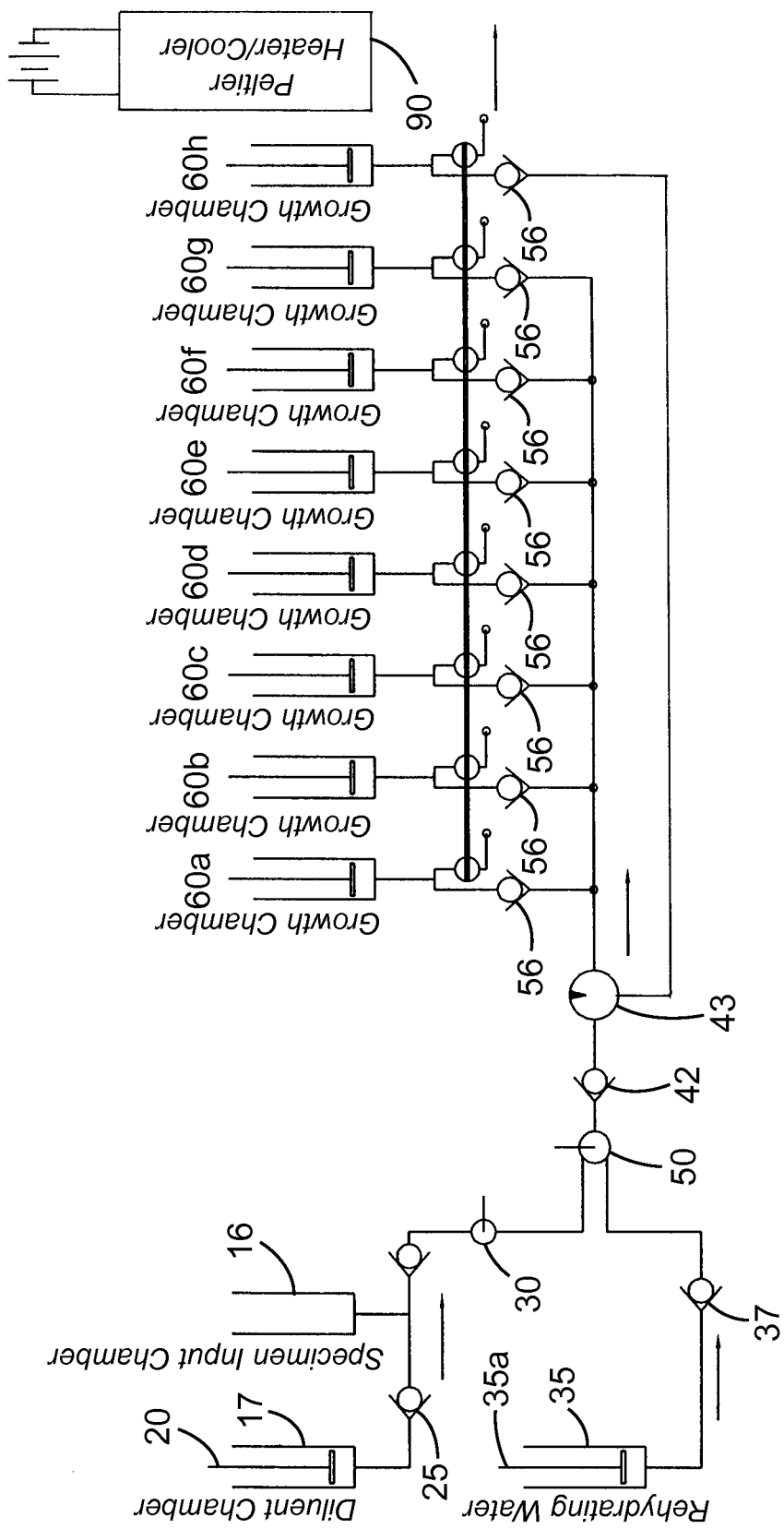
FIG. 4 illustrates one concept of the fluid flow schematic in the SCV of FIGS. 1-3.

The specimen input chamber 16 and the diluent chamber 17 both are coupled through small apertures in the top shell 11 to an input manifold 21. The input manifold 21 comprises a specimen port 22, a diluent port 23 and an output port 24, all connected by an internal fluid duct. An internal check valve 25 (see FIG. 4) in the fluid duct between the specimen input chamber 16 and the diluent chamber 17 prevents backflow of specimen into the diluent chamber.

The output port 24 of the input manifold 21 is fluidly coupled via flexible tubing (not shown) to a first T manifold 26, comprising first and second input ports 27, 28 and an output port 29 (all connected by an internal T-shaped fluid duct). Flow of the specimen/diluent mixture from the input manifold 21 to the first input port of the T manifold 26 is restricted by a shuttle valve mechanism 30. In one embodiment, this mechanism comprises a sliding shuttle 31, a cam 32 mounted on a rotatable shaft 33, and a finger-operable control handle 34. Upon rotation of the handle (which extends outside the SCV housing) by the operator, the shaft and cam are rotated, sliding the shuttle and thus opening or closing the valve mechanism 30.

A rehydrating water chamber 35 is fluidly coupled to the second input port of the T manifold 26 via flexible tubing (not shown) and an elbow manifold 36. The elbow manifold 36 comprises an internal fluid duct with a check valve 37 (see FIG. 4) to prevent the specimen/diluent mixture from back flowing to the water chamber 35. The water chamber 35 preferably contains distilled water for the purpose of rehydrating the culturing media in the growth chambers. In one embodiment, the amount of distilled water is 7.250 ml, plus an amount to make up for any dead volume losses. Optionally, the rehydrating water chamber has a plunger 35a (see FIG. 4) that is accessible on the exterior of the SCV housing by the operator, whereby the operator can selectively control the amount of water introduced into the system.

From the first T manifold 26, the specimen/diluent/water mixture flows via a flexible tube (not shown) to a second T manifold 38, comprising an input port 39 and first and second output ports 40, 41 (all connected by an internal T-shaped fluid duct). This second T manifold includes an internal check valve 42 (see FIG. 4) to prevent backflow of the mixture.

The pair of output ports 40, 41 in the second T manifold 38 feed the specimen/diluent/water mixture (via a pair of flexible tubes—not shown) into an actuator which facilitates the flow of the mixture throughout the SCV's fluid circulation system. In the embodiment illustrated in FIGS. 1-3, this actuator is a dual, low-pressure, rotary peristaltic pump 43 having a pair of input ports and a pair of output ports. As is well-known in the art, a peristaltic pump comprises a flexible tube fitted inside a circular pump casing, and a rotor with one or more rollers (or wipers) that intermittently compress the flexible tube as the rotor turns. The portion of the tube under compression closes, thus forcing fluid inside the tube to be pumped through the tube to an outlet port of the pump. As the tube opens to its natural state after the passing of a roller, fluid flow is induced into the inlet port of the pump. A dual peristaltic pump, such as used in the present embodiment, has a pair of compressible tubes and a pair of different rotor mechanisms, thus permitting pumping of fluids at two different rates as the rotors turn.

The rotors of the dual peristaltic pump 43 are driven by a crank mechanism 44 having a drive shaft 45 and a crank handle 46 mounted on the surface of the SCV housing. When the operator turns the crank handle in a clockwise direction, the rotors turn and the specimen/diluent/water mixture is drawn through the pump. It will be noted in the illustrated embodiment that flow of both the specimen/diluent mixture and the rehydrating water via separate flexible tubes to the first T manifold 26 (and then on to the second T manifold 38 and the peristaltic pump 43) is restricted by a dual shuttle valve 50. This valve is only opened upon turning by the operator of the crank mechanism 44 (specifically, by the rotation of a tumbler 47 attached as part of the crank mechanism and its resultant movement of the shuttle valve's armature 51, cam mechanism 52 and shuttle 53). Accordingly, it is impossible for any of the specimen/diluent mixture or the rehydrating water to reach either the pump or the growth chambers until the operator actuates the SCV by turning the crank mechanism 44.

In an alternate embodiment (not shown), the SCV includes a rotary motor within the housing and a rotatable crank mechanism coupled between the motor and the peristaltic pump. Thus, rather than being operated by hand-cranking, the pump is operated when the motor is powered. Power for the motor can be supplied either by a battery source within the SCV housing or by a source external to the housing (such as by plugging the SCV into a vehicle power source during transport). It will also be appreciated that the SCV can comprise other types of pumps well known to persons skilled in the art.

Specimen/diluent/water mixture exiting the first output port of the pump travels via a flexible tube (not shown) to a first inlet of a growth chamber manifold 55. In this manifold, the first inlet connects to a first fluid duct which branches into seven separate ducts (each with its own backflow-preventing check valve 56—see FIG. 4), whereby the specimen/diluent/water mixture is directed to as many as seven of the eight growth chambers 60a-g. Likewise, specimen/diluent/water mixture exiting the second output port of the pump travels via another flexible tube (not shown) to a second inlet of the growth chamber manifold 55. The second inlet connects to a second fluid duct (with its own backflow-preventing check valve 56) which directs the specimen/diluent/water mixture to the eighth of the eight growth chambers 60h. Ideally, the eight growth chambers are visible to the operator through an orifice 70 in the top shell 11 of the housing so that the integrity of the media within the chambers can be observed and the amount of specimen/diluent/water mixture introduced into the chambers can be observed and controlled.

In one embodiment of the SCV, the eight growth chambers consist of one specifically for viral culture and six or seven chambers for bacteriology or mycology. If only six chambers are utilized for bacteriology or mycology, the remaining chamber is saved for future expansion and does not contain culturing media. The viral growth chamber contains, preferably, 0.50 ml of specimen and liquid media, specifically for viral culture (total volume is determined as follows: 0.25 ml liquid media+0.25 ml specimen). The other seven growth chambers can contain, preferably, 1.05 ml of specimen and liquid media (total volume is determined as follows: 1.00 ml liquid media+0.05 ml specimen). More specifically, the SCV contains media suitable for the preservation and cultivation of all pathogenic bacteria, mycology, and viruses. The media selected for the SCV meets the criteria of encouraging growth in a maximum amount of organisms with a minimum number of separate media. The culturing media does not consist of caustic or dangerous chemicals which will hinder the operation of the SCV, and for PCR considerations the media does not contain any DNA or RNA fragments, or dead organisms. The media, when liquid, is transparent, which is necessary for turbidity checks (or other growth checks).

Preferably, the media contained in the growth chambers of the SCV comprises Tryptic Trypticase Soy Media; Tryptic Soy Agar w 5% Sheep Blood; Thioglycollate Media; Chocolate II Agar; BCYE Agar Base; Viral Transport Medium; Selective 7H11 Agar; as separate media, or as any mixtures thereof. As will be appreciated, SCVs can be manufactured with different combinations of growth media, thus providing different culturing choices to an operator to best match the circumstances of a particular biospecimen collection occurrence. The media is preferably lyophilized. Once rehydrated, the media has the proper pH. Optionally, one of the growth chambers (specifically the chamber containing Thioglycollate media) has the capability of having the oxygen removed from the chamber to promote the growth of anaerobic organisms. The other growth chambers (all except the one containing Thioglycollate media) should contain enough oxygen to promote the growth of aerobic organisms.

The SCV is manufactured sterile or the SCV is sterilized prior to leaving the manufacturing facility. The culturing media and diluent are dispensed into the SCV during the manufacture of the SCV. Importantly, the culturing media is sterile when inserted into the growth chambers of the SCV, or the media is sterilized during the SCV sterilization process mentioned above.

The SCV includes eight extraction portals—in the form of an eight-node plate 80 (each node backed by a flexible septum 81 penetrable by a hypodermic needle)—that allow media containing the specimen sample to be withdrawn quickly and easily. These portals also allow multiple samples to be drawn over a period of time. Each of the portals is connected fluidly to a separate one of the eight growth chambers 60*a-h* via respective flow ducts in the growth chamber manifold 55, eight flexible tubes (not shown), and respective flow ducts in an output manifold 82. An output shuttle valve 83 simultaneously controls the flow of specimen/media samples through the eight flexible tubes. Samples therefore can only be extracted from the SCV when the valve handle 84 and connected cam mechanism 85 have been rotated 90°, thus permitting the shuttle 86 to slide and opening the flexible tubes for fluid flow from the respective growth chambers. The valve handle 84 is configured and positioned so that it can be manipulated by either a human operator or a robotic unit in an automated analyzing platform.

Optionally, the SCV is equipped with one or more indicators that show if temperature, pressure, aerobic/anaerobic conditions, shock exposure, and radiation exposure tolerances have been breached. Moreover, the SCV can have some type of indicator (e.g., broken safety seal) to notify the user of potential contamination of the device prior to use.

The internal temperature of each of the growth chambers can be dynamically adjustable to promote optimum growth of the microorganisms. In that case, each growth chamber may have a temperature sensor, and there is an electronic feedback loop for the purpose of maintaining a specific temperature range (in other words, a thermostat or similar device).

The SCV also has at least one electrically powered "heater" and/or "chiller", for the purpose of creating an optimum growing environment. Preferably, this heater or chiller is a well-known type of solid-state thermoelectric module, such as a Peltier device 90 (see FIG. 4). Accordingly, the SCV requires a power source for any sensors, any associated LEDs, and the heater or chiller. In one embodiment, the SCV does not require external power sources, and all on-board electronic devices and batteries preferably have a shelf life greater than 12 months. In an alternate embodiment, the SCV has a power port which can readily be connected to an external power source (such as a portable battery or a vehicle power outlet).

The SCV is marked with a unique labeling that establishes the relationship of the patient and ordering event to the specimen acquired. This labeling can include conventional barcode, RFID tagging, similar techniques, or combinations thereof. For a barcode identification system, the HIBCC Standard is generally followed. For an RFID identification system, appropriate standards can be followed from ISO/IEC, IEEE and ANSI. An RFID tag preferably contains a data storage medium that will allow digital data to be written to it, stored on it and read from it, as defined by the version of the data storage medium.

This identification "links" the particular specimen and the results of its analysis to the original patient, source, and presumptive diagnosis. The orders placed for analysis and the corresponding results are linked to the analysis of the SCV contents and either stored with the specimen and/or transmitted via interface to a host information system, such as a Laboratory Information System (LIS) or Laboratory Information Management System (LIMS) that will store the patient demographics and test results or forward these results and patient demographics to other interfaced systems.

The minimum identification information required by the microbiology laboratory and MAP on the SCV is preferably stored in human-readable (e.g., label) form, as well as in digital format. For example, a label on the SCV should contain, for traceability purposes, some or all of the following: information regarding lot number, serial number, product identification number, manufactured date and expiration date. And the label on the SCV should have an area on which an operator can hand write data. The handwritten portion of the SCV's label should include space for a patient name, a patient unique identifier or date of birth, the collection time and date, the name of the person collecting the specimen, and the specimen type.

The information stored digitally on the SCV is preferably accessible in the absence of the MAP by means of devices such as PC-based or hand-held readers.

Communication to the SCV is performed through the SCV's identification system. The SCV's identification system comprises two parts: one that is physically attached to the SCV at all times and another part that can read or acknowledge the existence of the part attached to the SCV. The communication to the SCV follows approved standards of communication.

The SCV is designed for single use, and is preferably disposable. Thus, the SCV should be capable of being sterilized for disposal using standard laboratory methodologies (such as by lethal ionizing radiation). Sterilization of the SCV should not degrade the SCV's construction materials, valving or internal mechanisms, nor should it hinder the readability of the written or digital information stored thereon. The SCV can be disposed by using standard laboratory methodologies, including incineration.

Figure 5:
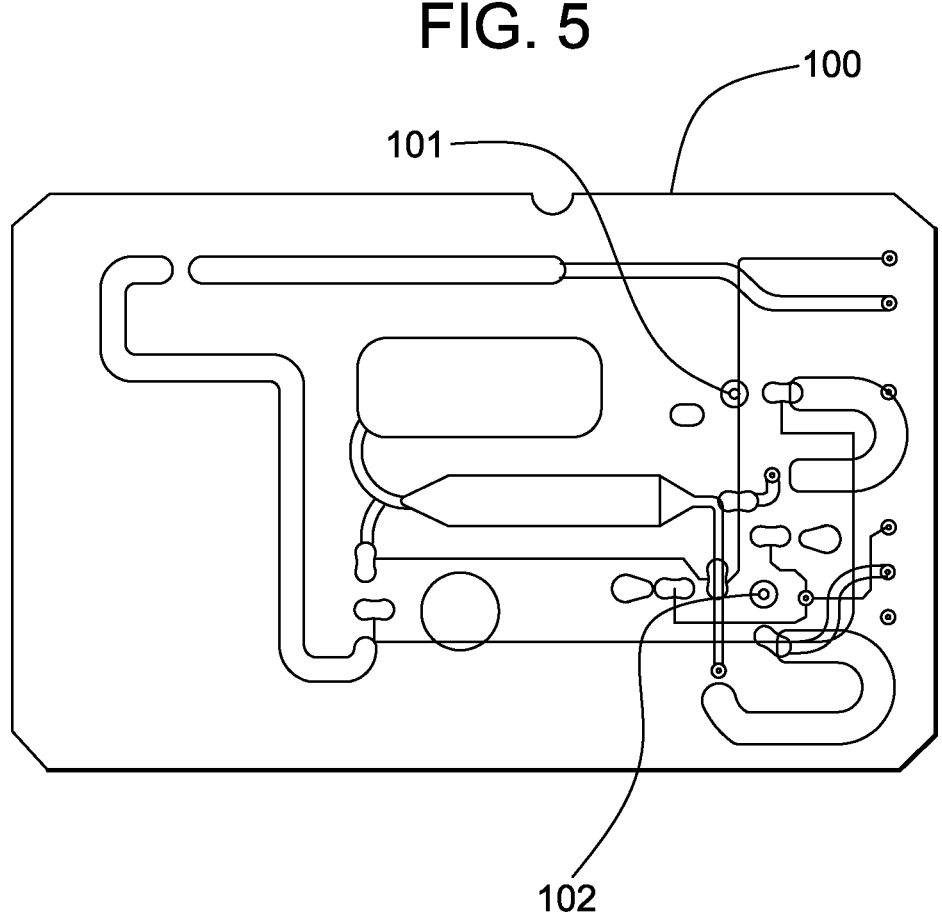
FIG. 5 illustrates an embodiment of a micro-lab plate that can be used in another embodiment of the SCV.

In an alternative embodiment of the SCV, rather than having growth chambers of the type shown in FIGS. 1-3, slots are provided within the housing for receiving a plurality of micro-lab plates (such as are available commercially from Micronics, Inc.). The plates either can be preselected and installed in the SCV during manufacture or can be "field" selected so that an operator can spontaneously configure the SCV to best fit the circumstances of a biospecimen collection occurrence. Each plate 100 (FIG. 5) comprises an inlet port 101 that, when the plate is installed within the SCV, fluidly connects to one of the fluid ducts within the SCV's growth chamber manifold 55, at least one outlet port 102 that fluidly connects to one of the SCV's extraction portals, and a series of interconnecting channels and chambers between the inlet and outlet ports for containment of culturing media and other substances deemed useful for the growth and preparation of the biospecimen. For example, appropriate substance can be provided in a plate to de-salt the cultured biospecimen (thus rendering it more suitable for subsequent mass spectrometry analysis).

The SCV is intended to integrate to an automated analyzing platform. The devices and methods of the present invention therefore preferably include a Microbiology Automation Platform (MAP) and microbiology analyzers and the platform to which they interface. The MAP of the present invention is meant to automate the processes of the user (operator) whether or not there is physical hardware in place to do the actual manipulation of the cultured biospecimen. Workflow logic determines and drives the series of steps required for a particular specimen. Various workstations perform the designated procedure on the specimen and return it to the control of the platform following the procedure. The workstations can optionally be an automated instrument or a human user (e.g., medical technician). In one example, the microbiology automation platform is a hybrid of a traditional Laboratory Information System (LIS) and a laboratory device. The platform receives orders and order updates from an LIS and sends results to an LIS, but it does not manipulate patient information or perform other functions traditionally performed by an LIS. It is possible to transmit data from the platform to national databases for the tracking of pathogenic outbreaks and trends in infectious diseases. Such systems are associated, for example, with State Health Laboratories, Health and Human Services at the state and national level, and the Centers for Disease Control and Prevention databases.

The SCV is designed with a physical feature that ensures proper orientation into the MAP. More specifically, the SCV has an elongated slot 88 formed extending across the bottom shell 12 of the housing (see FIGS. 1 and 3) that ensures its proper orientation on a conveyor track 110 used to automatically move one or more SCVs to and through various analyzing workstations 111-114 within the MAP. When the SCV is properly oriented in the MAP, the data storage medium (i.e., barcode or RFID tag) is accessible to and readable by appropriate identification readers, the eight extraction portals on the SCV are accessible to the medical device workstations performing the preparatory or analysis steps, and the valve handle 84 on the SCV is easily accessible and manageable by robotic units in the MAP, as well as by manual operation.

The graphic presentation of data on the MAP preferably includes: a Windows®-based color GUI, message logging, status reporting, trending, management reports, epidemiology reports, images, inventory, quality control, and instrument utilization reports. The MAP preferably supports within the same configuration multiple pre-processing components, multiple detection components, multiple identification components, and multiple susceptibility components.

Referring now to FIG. 6, a schematic diagram of SCV (and biospecimen) movement throughout the laboratory automation system is shown. This system operates as described in U.S. Pat. No. 5,614,415, the entirety of which is incorporated herein by reference. The SCV (with cultured biospecimen) arrives at a specimen receiving station 120, where the SCV is loaded onto a conveyor track system designated generally at 110. At specimen receiving station 120, the SCV is given an identification code which correlates with the SCV and the biospecimen to be analyzed, so that the SCV and biospecimen may be directed throughout the laboratory automation system, even when the SCV is removed from the conveyor track for specific testing at a workstation.

As shown in FIG. 6, conveyor track system 110 is preferably a continuously moving conveyor which will move SCVs in a generally closed loop system. At receiving station 120, the SCV assignment is entered into the MAP's CPU 130 to determine which workstations the biospecimen must utilize, the order in which the stations are to be utilized, the priority of the particular analyses to be conducted or steps to be taken, and any other pertinent information with respect to priority or turnaround time. Entry of this information may be as easy as scanning the RFID tag or barcode of the SCV. As represented by the double-headed arrows in FIG. 6, it will be appreciated that the CPU communicates (wirelessly or by hard wire connection) with each of the workstations 111-114 and the receiving station 120.

While FIG. 6 shows only four specific workstations 111-114, a conventional clinical laboratory could have a wide variety of such stations throughout a facility. The closed loop system of conveyor track 110 permits a biospecimen to stop at any given workstation in any desired order. Thus, if time constraints require that the analysis of workstation 113 be performed first, and that an analysis of workstation 111 be performed at some time after the analysis of workstation 113, the SCV containing the biospecimen can travel on conveyor track 110 past workstations 111 and 112, directly to workstation 113, for immediate analysis. The SCV is then reintroduced onto the conveyor track 110 to follow the closed loop around to the next workstation assigned to the biospecimen. Once all desired analyses have been completed, the SCV (with any remaining cultured or original biospecimen) is forwarded to a specimen archiving station 115 for removal from the conveyor track 110 and appropriate storage. The MAP supports the maintenance of a portion of the original biospecimen that is not contaminated or altered during processing and, therefore, is maintained for quality assurance purposes and/or confirmatory testing.

The dispensing of the biospecimen/media combination from the extraction portals on the SCV is preferably performed automatically by the MAP's workstation equipment (including robotic extraction probes or needles), but it can also be done manually. The MAP equipment checks specimen volume prior to testing to ensure sufficient quantity for the testing to be performed, and the MAP continuously tracks the amount of specimen processed from the SCV in order to determine availability of specimen volume for further testing. The MAP equipment also is capable of re-closing the SCV after specimen has been removed or reagents/diluents have been added.

The devices and methods of the present invention also include software. Thus, the MAP can be configured to perform many different functions, as desired by a particular clinical facility. For example, the MAP has the capability to dynamically change the processing steps to completion of the specimen analysis based on information either received with the order or through information associated with the current status of the specimen. The MAP is developed with a rules engine that drives the logic of processing steps based upon microbiology standards in practice. This rule set is user configurable to mimic the current standard operating procedures of the microbiology laboratory staff. The MAP has the capability of sending revised or additional orders to a host system through a standard data communications interface 135.

The MAP is developed with on-line specimen tracking. Specimen status is presented to the user interface in a graphical presentation. Specimen status preferably includes: estimated time of testing completion, turn-around-time reporting, logging of any event where the SCV is manually removed from the system, and a logging of the duration of time the SCV spends at any sub-process in the system.

The MAP records a complete processing history for each SCV processed, including maintaining the data relationship between the SCV (the primary specimen) and any aliquots (secondary specimens) that are created from the original SCV specimen. Data stored on the MAP are accessible remotely. The MAP contains an event monitoring, recording, and notification system.

The MAP software supports auto-verification of patient results. The MAP software automatically accepts or rejects a specimen result based on a series of user-defined rule sets. Rules for test scheduling and routing changes are customizable based on laboratory operational, business, and clinical objectives.

The MAP can optionally have the capability to automatically prepare specimen and accompanying paperwork to refer specimens to public health entities. Similarly, the MAP can optionally support the collection and reporting of data for peer-to-peer Quality Assurance programs (and thus can optionally have the capability of maintaining various Quality Assurance reports on-line).

It is to be understood that this invention is not limited to the particular devices, methodology, protocols, subjects, or reagents described, and as such may vary. It is also to be understood that the terminology used herein is for the purpose of describing particular embodiments only, and is not intended to limit the scope of the present invention, which is limited only by the claims. Other suitable modifications and adaptations of a variety of conditions and parameters, obvious to those skilled in the art of microbiological diagnostics, are within the scope of this invention.

The invention claimed is:

1. A portable apparatus for collecting and culturing a biospecimen sample containing biological organisms, comprising:
   a housing having an insertion portal and a plurality of extraction portals;
   a specimen input chamber enclosed within the housing and connected to the insertion portal so as to receive the biospecimen sample from outside the housing;
   a plurality of culture mediums;
   a plurality of culturing chambers enclosed within the housing, at least two of said plurality of culturing chambers containing respective contents including respective ones of said plurality of culture mediums, each of the plurality of culturing chambers being adapted to receive a portion of the biospecimen sample, and each of the plurality of culturing chambers being in fluid communication with a respective one of the extraction portals to permit access to the respective contents of the plurality of culturing chambers;
   a system of fluid ducts within the housing that connect the specimen input chamber to each of the culturing chambers; and
   an actuator that facilitates flow of portions of the biospecimen sample from the specimen input chamber through the system of fluid ducts and into each of the culturing chambers;
   wherein biological organisms in the biospecimen begin to grow in one or more of the culturing chambers and cultured portions of the biospecimen sample being accessible for selective withdrawal from the apparatus via the extraction portals.

2. The apparatus of claim 1, further comprising a first fluid chamber having a moveable plunger and containing a diluent, the first fluid chamber being connected via a flooding duct to the specimen input chamber, whereby flow of the diluent through the flooding duct and into the specimen input chamber is controlled by movement of the plunger.

3. The apparatus of claim 1, wherein at least one of the culturing chambers comprises a slot formed inside the housing and a micro-lab plate, having an inlet and an outlet, inserted into the slot so as to fluidly communicate at the inlet with a predetermined fluid duct and at the outlet with a predetermined extraction portal.

4. The apparatus of claim 3 in which the micro-lab plate further comprises means for de-salting the portion of the biospecimen sample received therein.

5. The apparatus of claim 1, further comprising means for controlling the temperature within the housing.

6. The apparatus of claim 5 in which the temperature-controlling means is a Peltier device located within the housing.

7. The apparatus of claim 1, further comprising means for identifying the source of the biospecimen sample.

8. The apparatus of claim 7 in which the identifying means is an RFID tag.

9. The apparatus of claim 7 in which the identifying means is a barcode tag.

10. The apparatus of claim 1 in which the actuator comprises a peristaltic pump connected to the system of fluid ducts within the housing, whereby upon operation of the pump portions of the biospecimen sample are induced to flow through the fluid ducts and into the plurality of culturing chambers.

11. The apparatus of claim 10 in which a rotatable crank mechanism is coupled to the pump and includes a hand grasp mounted on the exterior of the housing, whereby a user operates the pump by hand-rotating the grasp.

12. The apparatus of claim 10, further including a rotary motor within the housing and a rotatable crank mechanism coupled between the motor and the pump, such that powering of the motor rotates the crank mechanism and operates the pump.

13. The apparatus of claim 12 in which the motor is powered by a battery within the housing.

14. The apparatus of claim 12 in which a source external to the housing is used to power the motor.

15. The apparatus of claim 1, further comprising a second fluid chamber containing water, the second fluid chamber being fluidly connected to the culturing chambers, whereby flow of the water into the culturing chambers hydrates the culture media.

16. The apparatus of claim 1 further including a plurality of valves, at least one of said valves being associated with and controlling flow into or out of a respective one of each of the culturing chambers.

17. The apparatus of claim 16 wherein integrity of the contents of said at least a portion of the plurality of the culturing chambers is maintained regardless of the orientation of said housing.

18. The apparatus of claim 1 wherein the housing has a diameter on the order of 8.9 cm or smaller.

19. The apparatus of claim 1 wherein the housing is sized to fit in a biohazard transport bag.

20. The apparatus of claim 1 wherein the housing is sized to fit in a hospital pneumatic tube transport system.

21. The apparatus of claim 1 wherein the housing includes a bottom surface, the bottom including a generally flat portion.

22. The apparatus of claim 21 wherein the housing includes a top surface generally opposite the bottom surface, the top surface including a generally flat portion.

* * * * *